United States Patent [19]

Hasson

[11] 4,224,951
[45] Sep. 30, 1980

[54] GYNECOLOGICAL INSTRUMENT

[76] Inventor: Harrith M. Hasson, 345 Fullerton Pkwy., Chicago, Ill. 60614

[21] Appl. No.: 965,170

[22] Filed: Nov. 30, 1978

[51] Int. Cl.³ .............................................. A61B 5/10
[52] U.S. Cl. .................................. 128/778; 33/174 D
[58] Field of Search ............... 128/778, 737, 759, 780, 128/784; 33/174 D

[56] References Cited

U.S. PATENT DOCUMENTS

| 512,025 | 1/1894 | Haviland | 128/778 |
|---|---|---|---|
| 3,394,699 | 7/1968 | Koett | 128/759 |
| 3,491,747 | 1/1970 | Robinson | 128/757 |
| 3,706,307 | 12/1972 | Hasson | 128/778 |
| 4,016,867 | 4/1977 | King et al. | 128/778 |

Primary Examiner—Kyle L. Howell
Attorney, Agent, or Firm—George H. Gerstman

[57] ABSTRACT

A multi-purpose intra-uterine probe for sounding the depth of the fundus and measuring the width of the uterus at two different insertion depths. The latter objective is accomplished by an extendable wing mechanism having two stable wing-spreads selectable by means of a ball-point pen-type push-button control mechanism, and indicating windows which are color-coded in relation to the rotating push-button of the control mechanism to illustrate the proper sequence of read-out locations. A window reads out the depth of the fundus. The entire uterine probe assembly, including both the flexible wing-forming sleeve and the connecting rod which foreshortens the sleeve to collapse it into its wing configurations, is a disposable component which removably and replaceably connects to the handle assembly; the wing-forming sleeve connecting to the handle tube, and the foreshortening rod connecting to an actuating mechanism which reciprocates the rod relative to the handle tube, and hence relative to the wing-forming sleeve.

13 Claims, 21 Drawing Figures

GYNECOLOGICAL INSTRUMENT

BACKGROUND OF THE INVENTION

This invention is an improvement in the type of dual purpose gynecological instrument which is used both to obtain axial uterine measurements and to obtain a width profile of the uterus.

Instruments of this type are exemplified by the present inventor's own prior art U.S. Pat. No. 3,706,307. This patent shows an elongated uterine probe assembly comprising a rod cylindrically surrounded by a flexible plastic sleeve formed with short longitudinal slits. This probe is used to sound the entire depth of the uterus, i.e., the entire depth of the cervical canal and endometrial cavity, by inserting it to the depth of the fundus (the back wall of the uterus). It is also used to locate the position of the uterine isthmus or cervical isthmic region, and therefore to determine cervical length. The rod is retracted by a predetermined amount so as to foreshorten the plastic sleeve while the probe is still within the uterus. This causes the plastic sleeve to collapse laterally outwardly a predetermined distance to form radially extending wings. The slits formed in the sleeve facilitate this collapse. The probe is then withdrawn until the extended wings make contact with the walls of the uterus at the level of the uterine isthmus, preventing any further withdrawal, and the depth of the insertion is noted. This second measurement represents the effective length of the cervix which includes the cervical canal, isthmus and a variable small portion of the lower uterine segment.

While the aforementioned observation would tell the gynecologist that at that particular depth of insertion the uterus has a width equal to the predetermined "wing spread" of the instrument, it does not permit the gynecologist to extrapolate the shape or width dimensions of the uterine cavity on the basis of the fragmentary information obtained. Thus the instrument of the inventor's own prior art was designed essentially to determine individual axial uterine dimensions of total uterine length, and the length of the endometrial cavity by taking the cervical length and subtracting the cervical length from the whole uterine length. The instrument thus measures only axial dimensions and does not and is not intended to measure uterine width.

A uterine caliper which enables width measurements is disclosed in King, et al. U.S. Pat. No. 4,016,867. This caliper has outwardly biased resilient caliper wings and a spring-loaded slidable cervical stop. A slide on the body is operatively connected to the wings by a monofilament and operates with respect to a first scale on the body as a width indicator. The wings may be allowed to open by moving the slide, and when the wings engage the utero-tubal junctions, the width may be read on the first scale.

The present inventor has found that it would be desirable to have relatively complete information from which one can extrapolate the shape and width dimensions of the endometrial cavity. It would therefore be desirable to improve the depth-width probes described above so that they are capable of measuring axial uterine dimensions as well as the insertion depths at which the width of the uterus matches a plurality of different predetermined wing spreads of the expandable probe.

But in trying to accomplish that objective, a second problem arises. The prior art single width probe described above needs only a simple and inexpensive mechanism for retracting the foreshortening rod to a single stable position at which the wings collapse outwardly to the predetermined width. Consequently, the entire instrument, including both the probe and the wing-actuating mechanism therefor, is economically disposable.

However, a multiple-position wing actuating mechanism is necessarily more complex and expensive than its single-position prior art counterpart. Therefore, with an improved probe of the kind contemplated herein there would be considerable reluctance to dispose of the entire instrument, including the more expensive wing-actuating mechanism. It would be desirable, instead, for the probe assembly to be removable and replaceable so that it alone is disposable, and the actuating mechanism is not.

There is one further complicating factor. Recall for a moment that the probe assembly consists of two separate parts, the collapsible sleeve and the foreshortening rod, which must be movable relative to each other in order to accomplish the foreshortening operation which expands the wings. Thus the provision for removable and replaceable connection of the disposable probe assembly to the permanent portion of the instrument must somehow connect these two probe components to two respective independently movable parts of the permanent assembly.

BRIEF SUMMARY OF THE INVENTION

The present invention addresses these problems by providing an intra-uterine probe instrument which is capable of expanding the probe sleeve wings to more than one predetermined measuring width, thus providing the gynecologist with important additional width profile information from which to extrapolate the shape and size of the endometrial cavity, using the conventional graphing technique. It does so, however, without sacrificing the concept of probe disposability. In the present invention, the probe assembly is removable and replaceable; the probe sleeve component thereof removably interengaging with the handle assembly, and the foreshortening rod component thereof removably interengaging with the wing actuating link.

Multiple extension positions of the probe wings necessarily require an actuating mechanism capable of holding a plurality of stable positions; and to accomplish this most expediently, the well known spring-loaded, rotary-cam, push-button mechanism is adapted from the ball-point pen environment and put to use in the present invention.

The instrument of this invention therefore takes at least three separate readings: total uterine length, plus depth insertion at two or more different uterine widths; including one indicating the position of the isthmus or cervical isthmic region. Accordingly, at least three separate pointers are provided, which are calibrated to indicate respectively the entire depth of the endometrial cavity and cervical canal (full probe insertion) and at least two partial insertion depths at which the uterine width corresponds to different wing expansions. Different surfaces of the ball-point pen-type control push-button are rotated into alignment with these read-out pointers during different operating conditions of the instrument; and matching sets of markings, located on these push-button surfaces and adjacent to the pointers, indicate the appropriate pointer from which to take the reading at each successive stage of the uterine measurement procedure.

Another advantage of the present invention relates to a reading tube. In the inventor's prior art device, the reading tube had to be advanced manually with each of the two readings (total length and cervical length) to abut the cervix. This was cumbersome and required the use of two hands to accomplish the reading or application. The need to advance the reading tube manually is eliminated by the present invention; the sleeve is actuated by a spring that tends to push the sleeve forward to abut the cervix automatically, but it can be locked in any position on the handle by a locking collar when desired.

Finally, modified wings of the probe sleeve of the present invention can optionally be used as tissue scraping scoops or as curette tips for uterine cancer screening, early stage abortion or other curettage procedures.

Other objects and advantages of the present invention will become apparent as the description proceeds.

DETAILED DESCRIPTION OF THE ILLUSTRATIVE EMBODIMENT

Figures 1, 2, 3:
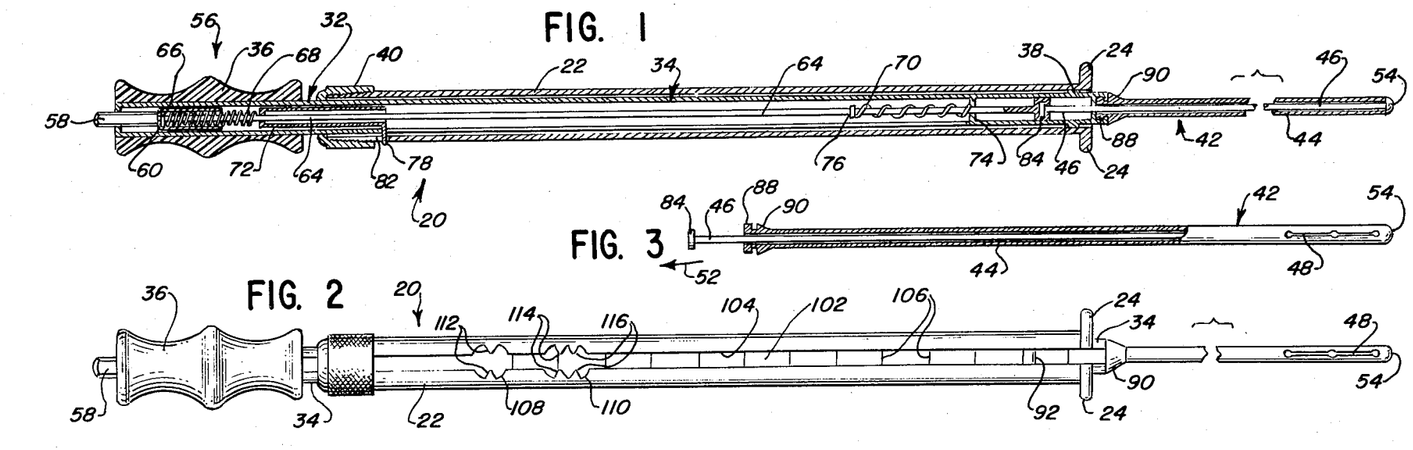
FIG. 1 is a longitudinal section of an instrument in accordance with this invention, shown with the removable probe assembly in place.
FIG. 2 is a top elevation of the same instrument, in the same condition.
FIG. 3 is an elevation of the probe assembly alone, with parts sectioned.
Figure 7:
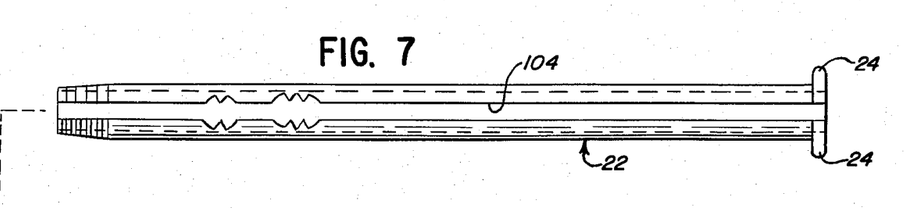
FIG. 7 is a top elevation of the reading tube of this instrument.
Figure 8:
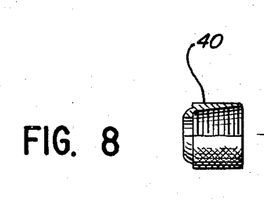
FIG. 8, which is in exploded relation to FIG. 7, is a section of the locking ring of this instrument.

The gynecological instrument of this invention, generally designated 20 in FIGS. 1 and 2, comprises several distinct parts and subassemblies. The first of these is a reading tube 22 (seen as part of the overall assembly in FIGS. 1 and 2 and again in isolation in FIGS. 7, 9 and 10), which serves as both a reading sleeve and a cervical stop of the instrument. The reading tube 22 is a hollow cylindrical member made of a durable material, such as a plastic polymer. At a distal end of the reading tube 22, it is formed with opposing flanges 24 which abut the end of the cervix 26 to provide a cervical stop (see FIG. 18) which limits insertion of the tube 22 into the cervix and determines the position of the external cervical OS. These flanges 24 establish a reference plane 28 coincident with the end of the cervix 26, from which a plurality of measurements of depth of insertion of the instrument into the uterus 30 may then be taken.

Figures 11, 12:
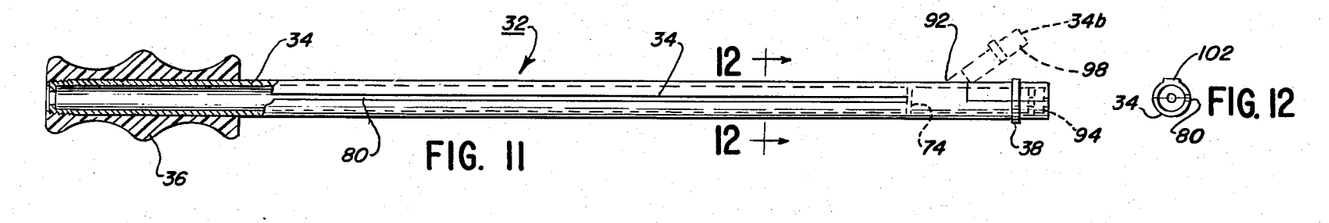
FIG. 11 is a side elevation, with parts sectioned, of the handle and handle tube of this instrument.
FIG. 12 is a section, along the lines 12—12 of FIG. 11, looking in the direction of the arrows, of the handle tube of this instrument.
Figures 13, 14, 15, 20:
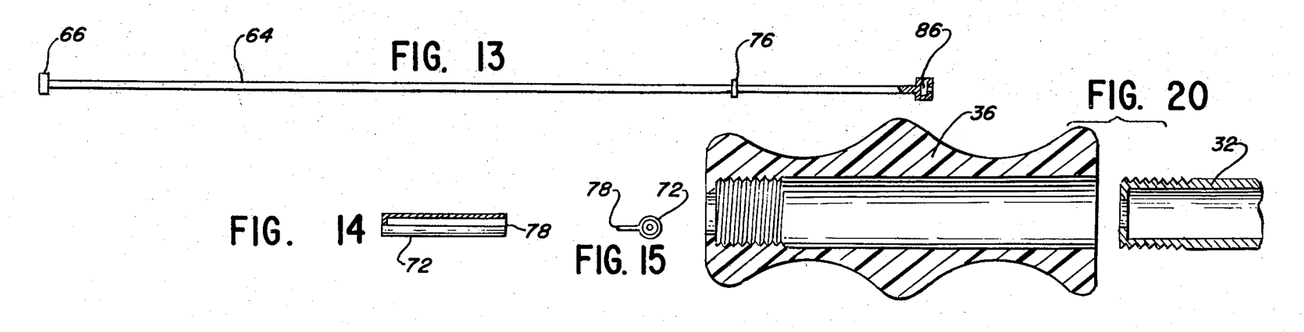
FIG. 13 is an elevation, partially sectioned, of the wing-actuating rod of this instrument.
FIG. 14 is a side elevation, with parts sectioned, of the pin cylinder of this instrument.
FIG. 15 is an end elevation of the same pin cylinder.
FIG. 20 is a cross-sectional exploded view of a portion of the handle assembly.

The reading tube moves slidably over a handle assembly generally designated 32 and seen in isolation in FIG. 11. The handle assembly includes a handle tube 34 and a handle 36. The handle tube 34 serves as the main chassis of the instrument. The tube 34 is preferably made of durable, rigid material, such as stainless steel. The handle 36 is attached to the proximal end of the tube 34 by a threaded connection (see FIG. 20) and the distal end of the tube 34 is received within the interior of the reading tube 22. Two structures provide bearings which support the handle tube 34 so that the entire handle assembly 32 easily slides longitudinally relative to the reading tube 22. These are: first, an external restraining flange 38 which is formed near the distal end of the handle tube 34 and which contacts the inner walls of reading tube 22; and second, a metal locking collar 40 which surrounds the proximal end of the reading tube 22 and which has internal conical threads mating with external conical threads on the adjacent portion of the reading tube 22. This collar 40 has an opening through which the handle tube 34 passes, and which thus serves as a bearing for the longitudinal reciprocation of the tube 34.

Collar 40 moves independently over the handle tube 34 as does reading tube 22. Reading tube 22 can leave the handle tube, but collar 40 cannot be removed from the handle tube due to flange 38 which causes an interlocking or restraining engagement with the conical portion of the collar.

Figures 6, 6A:
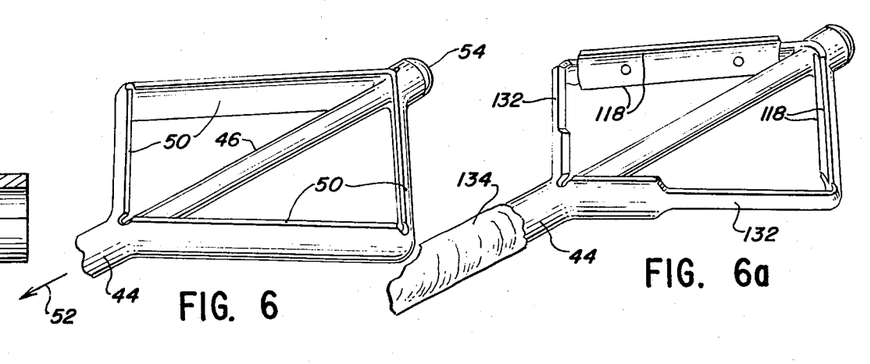
FIG. 6 is a perspective view of the wings at the tip of the probe assembly, seen in expanded condition.
FIG. 6A is a similar view of the expanded wings in an alternative embodiment of the invention, wherein the wing surfaces are formed for performing certain special functions, such as taking cellular samples for the "Pap" smears or for curettage.

The next major subassembly to be described is the probe assembly 42, seen in isolation in FIG. 3. This includes a wing-forming sleeve 44 and a foreshortening rod 46 which is received within the sleeve 44. The sleeve is formed of a thin, flexible plastic material, and is provided with short longitudinal slits 48 on opposite sides. These slits serve to define panels 50 which are free to fold and bend or collapse radially and outwardly to form opposed wing structures, as illustrated in FIG. 6, when the sleeve 44 is forcibly foreshortened. Such foreshortening is accomplished by moving the foreshortening rod 46 longitudinally rearwardly relative to the sleeve 44, as indicated by arrows 52, whereupon an enlarged tip 54 formed on the distal end of the rod 46 exerts the necessary foreshortening force on the sleeve 44. Rod 46 is made of fairly rigid material, such as metal or fairly rigid plastic.

Figure 4:
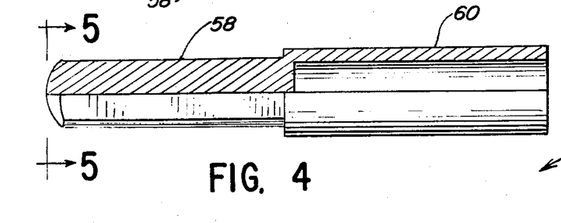
FIG. 4 is a top or side elevation, with parts sectioned, of the push-button which controls the ball-point pen-type actuating mechanism for the expandable probe wings.
Figure 9:
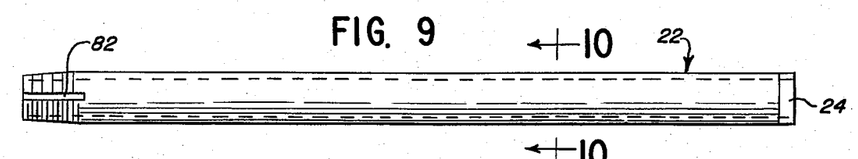
FIG. 9 is a side elevation of the same reading tube.
Figure 10:
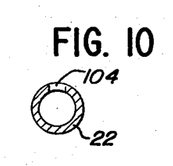
FIG. 10 is a section of the reading tube taken along lines 10—10 of FIG. 9, looking in the direction of the arrows.
Figure 16:
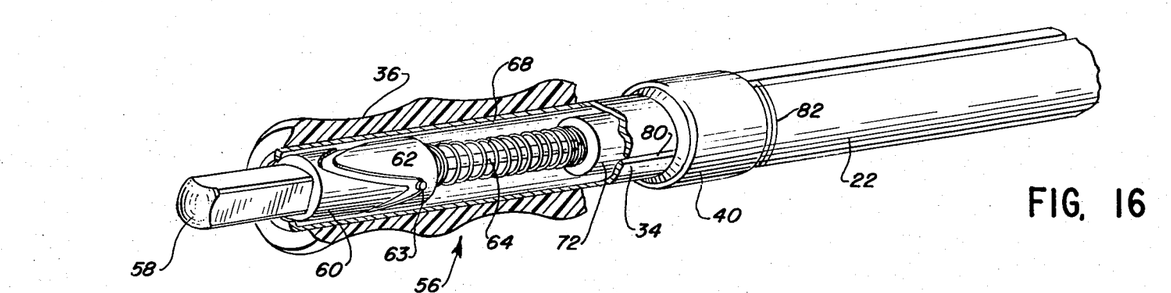
FIG. 16 is a perspective view, with parts broken away for clarity, of the wing-actuating mechanism of this instrument.

The next major subassembly to be considered is the wing-actuating mechanism, generally designated 56 in FIG. 16, which controls the described longitudinal motion of the foreshortening rod 46 in order to determine when the wings 50 will and will not be extended. This mechanism 56 is a conventional push-button operated rotary cam movement of the type now familiar in retractable ball-point pens. The control push-button 58 projects from the proximal end of the handle tube 34, and is molded integrally with a cylindrically shaped rotary cam barrel 60 (see in particular FIG. 4). The outer surface of the cam barrel 60 is formed with a sinuous cam track groove 62 (FIG. 16) which is engaged by a short cam pin 63 extending radially inwardly from the inner wall of the handle tube 34. Received within the hollow interior of the cam barrel 60 is the proximal end of a wing-actuating link 64 (see also FIG. 13) and a flange 66 formed thereon. A first biasing spring 68 surrounds the proximal end of the actuating link 64, and a second biasing spring 70 (FIG. 1) surrounds the distal end. The first spring 68 reacts between the interior of the cam barrel 60 and the closed end of cylinder 72, while the second spring 70 reacts between a flange 74 formed on the interior wall of the handle tube 34 and a flange 76 formed on the surface of the actuating link 64. The cylinder 72 surrounds the link 64 and is connected to the reading tube 22 by means of a radially extending pin 78 (see FIGS. 14 and 15). The pin extends through an elongated clearance slot 80 formed in the handle tube 34 (FIGS. 1, 11, 12 and 16) and reaches into a much shorter slot 82 formed in the reading tube 22 (FIGS. 1, 9 and 16).

Slot 82 serves to trap pin 78 in reading tube 22, thereby attaching cylinder 72 powered by biasing spring 68 to reading tube 22, biasing the tube distally. Pin 78 is held in place in slot 82 by metal collar 40. However, the entire assembly can slide over the handle tube 34 unless collar 40 is engaged fully, crimping the conical threads of the reading tube into the handle tube 34 and thus immobilizing the reading tube assembly. Thus the elongated slot 80 simply provides clearance around the pin 78 for the reciprocating motion of cylinder 72 and the attached reading tube assembly 22 relative to handle tube 34.

In this ball-point pen-type of actuating mechanism 56, the actuating link 64 plays the role of the ball-point pen refill; that is to say, the effect of the mechanism 56 is to reciprocate the link 64 longitudinally between a plurality of stable positions (such as the extended and retracted positions of the refill in the familiar retractable type of ball-point pen). Each stable position of the actuating link corresponds to a relative maximum or relative minimum in the sinuous curve of the cam track 62. Here the purpose of the reciprocation of the actuating link 64 is to determine the operating positions of the foreshortening rod 46.

As the actuating link 64 is reciprocated by the mechanism 56, it moves relative to the handle tube 34. Since it must drive the foreshortening rod 46 with it, there must be a driving connection between the link 64 and rod 46. In order to guarantee that the rod 46 and its tip 54 then move the distal end of the wing-forming sleeve 44 closer to its proximal end in order to produce the foreshortening effect, the proximal end must be anchored to the handle tube 34. To preserve the concept of disposability, the probe assembly 42 is made readily removable and replaceable relative to the handle assembly. The entire instrument 20 is divided into a permanent portion, comprising the reading tube 22 and the handle assembly 32, and a disposable portion, comprising the probe assembly 42 (sleeve 44 and rod 46). Therefore, the drive connection between the rod 46 and the link 64, as well as the anchoring connection between the sleeve 44 and the handle tube 34, is preferably of the removable and replaceable type.

Figure 17:
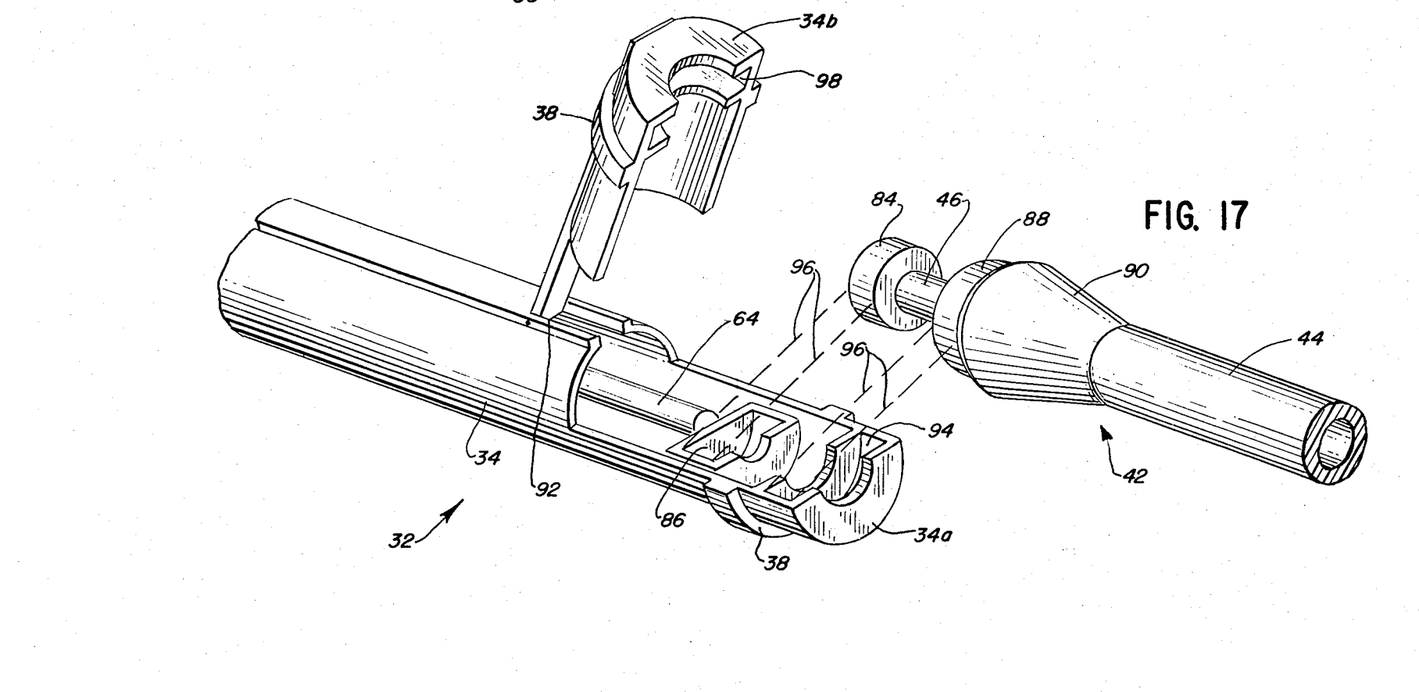
FIG. 17 is an exploded perspective view of the removable and replaceable interengaging parts of the probe assembly, handle tube and wing-actuating mechanism.

To accomplish this, as seen in FIGS. 1, 3 and 17, the proximal end of the rod 46 is formed with a drive flange 84, and the distal end of the link 64 is formed with a receptacle 86 designed to receive the flange 84. Similarly, the proximal end of the sleeve 44 is formed with an anchoring flange 88, spaced a short distance proximal to a conically-shaped enlargement 90 which is also formed on the sleeve 44. The distal end of the handle 34 is bifurcated to form a fixed half 34a, and a hinged half 34b which swings radially outwardly.

The fixed half 34a is formed with a receptacle 94 into which the sleeve anchoring flange 88 fits. The hinged half 34b swings away to permit the flanges 84 and 88 to be inserted laterally into the receptacles 86 and 94. A pin hinge at 92 provides the required hinge structure with the pin hinge preferably being made of metal.

The direction of insertion of flanges 84 and 88 into their respective receptacles 86 and 94 is indicated in FIG. 17 by the dashed lines 96. The hinged half 34b is also formed with a receptacle 98 which closes over the sleeve flange 88, after its insertion into the receptacle 94, upon closing of the hinged half 34b. After such closure, the hinged half 34b serves to retain the flanges 84 and 88 in their respective receptacles 86 and 94 so that the probe assembly 42 remains properly assembled with the handle assembly 32, with reading tube 22 normally covering and splinting the distal bifurcated end of handle tube 34 thus retaining it in position. Subsequently, however, the probe assembly may be removed and replaced.

When using the instrument 20, the gynecologist begins by loading a probe assembly 42 into the receptacles 86 and 94, and closing the hinged half 34b. Reading tube 22 is then slid rearwardly over tube 34, until the threaded portion of the reading tube 22 engages pin 78 in slot 82 and metal collar 40 which is carried on tube 34. The reading tube is naturally aligned so that pin 78 enters slot 82 and then collar 40 is tightened on the threaded portion of reading tube 22, thus temporarily locking reading tube 22 in a proximal position over handle tube 34.

Figures 18, 19:
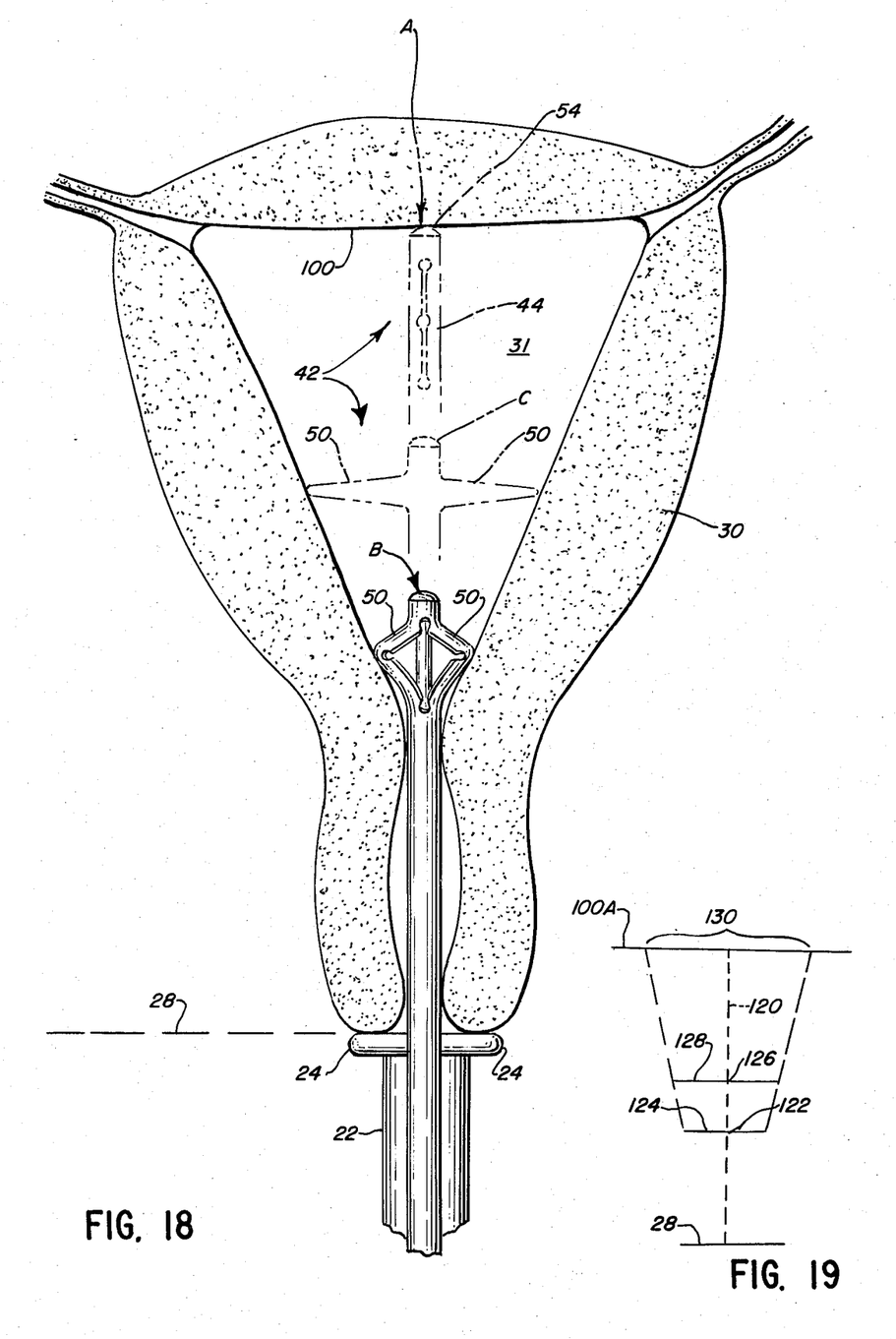
FIG. 18 is a sectional view of a uterus, plus multiple elevational views of a probe in accordance with this invention inserted therein, the multiple views showing the probe in three different operating positions within the uterus for taking three separate uterine measurements.
FIG. 19 is a diagrammatic view of a method of extrapolating uterine dimensions using the present invention.

The distal end of the instrument 20 is introduced into the vaginal canal, and the probe assembly 42 is inserted through the cervical canal into the endometrial cavity 31 until the probe tip 54 touches the fundus 100, as indicated at A in FIG. 18. Collar 40 is then loosened, releasing reading tube 22 which then moves distally over handle tube 34 by means of spring 68, cylinder 72 and pin 78 cooperating with slot 82 of reading tube 22, until the tube flanges 24 abut the end of cervix 26. In this position, a measurement may be taken of the overall length of the uterus 30 and cervix 26, for example, from the reference plane 28 to the fundus 100. Reading tube 22 then remains abutting the cervix as long as metal collar 40 remains loosely attached to reading tube 22.

The necessary longitudinal measurement is achieved by means of a flat, raised longitudinally extending key 102 (FIGS. 2 and 12) which is formed on one side of the handle tube 34, and rides in a mating keyway or slot 104 (FIGS. 2 and 7) formed in the reading tube 22. The face of the key is visible through the keyway, and on that face there are distance markings 106 (FIG. 2) which represent the depth of insertion of the probe assembly 42 into the uterus 30. At appropriate places the keyway 104 widens into read-out windows 108 and 110 equipped with three pairs of pointers 112, 114 and 116, respectively, for taking various probe depth insertion readings. The pointers 112 in window 108 are used for taking the fundus sounding measurement, which indicates the overall length of the uterus and cervix.

During the overall length measurement described above, actuating link 64 is maintained by the cam barrel 60 in a stable position calculated to keep the foreshortening rod 46 and probe sleeve 44 fully extended, so that the wings 50 are not expanded, thus permitting the initial insertion of the probe into the uterus. The position of the pointers 112 which are used in taking the overall depth reading, moreover, is calibrated with reference to the fact that the length of the probe assembly is maximal during the overall depth measurement, because of the fact that the rod 46 is located fully forward.

But after the overall depth measurement is completed, the push-button 58 is operated, partially retracting the link 64 to another stable position established by the cam barrel 60. In this latter position, the rod 46 is retracted to partially foreshorten sleeve 44 and partially extend the wings 50 so that the wings are expanded but not fully so. The probe assembly 42 is then withdrawn, by sliding the entire handle assembly 32 rearwardly relative to the reading tube 22, until the expanded wings 50 abut the sidewalls of the uterus 30 and become impacted in the area of the isthmus (position B in FIG. 18). The position of the cervical isthmus region is then known and its width is determined to be equal to the predetermined partial wingspread of wings 50. That insertion depth represents the effective length of the cervix which includes the cervix and isthmus and a small variable portion of the lower uterine segment. Effective cervical length can now be read off against the scale markings 106 on the face of the key 102. But for this reading, a different set of pointers 114 (appearing in the more distal window 110) must be used; these pointers are in a different higher location, which is calibrated with respect to the shorter overall probe length resulting from the retraction of the foreshortening rod 46 when the wings 50 are expanded and the ensuing distance between the collapsed expanded wings and distal end 54. Endometrial cavity length can then be determined by subtracting the cervical length from the initial total uterine measurement. However, if the cervix is partially or totally incompetent, the probe 42 with its partially expanded wings 50 will not stop at this level, but will continue to slide through the cervix out into the vagina. The width and relative competence of such a cervix can then be calibrated and assessed by actuating push-button 58 so as to extend wings 50 more fully or to attach other disposable probe assemblies with inherently greater wing expansion capabilities as described below.

To extrapolate the uterine shape and width profile, one or more additional width measurements may be taken. The push-button 58 is actuated once again moving the actuating link 64 to another stable position established by the cam barrel 60. In this position, the foreshortening rod 46 and the probe sleeve 44 are fully extended so that the wings 50 are not expanded. The probe 42 is inserted deeper into the endometrial cavity 31 and the push-button 58 is again actuated to move actuating link 64 to another stable position established by cam barrel 60. In this position, the foreshortening rod is maximally retracted. Therefore, the wings 50 are fully expanded. Thus the wing spread equals a second predetermined uterine width, greater than that used in the first width measurement described above. Since the wing spread is greater, the probe cannot be withdrawn to the level of the isthmus, but stops at a higher level. This withdrawal of the probe proceeds until the greater wing spread again abuts the sidewalls of the uterus 30 at a higher, wider location, e.g., position C in FIG. 18. The greater insertion depth at which this occurs can again be read off the scale 106, but this time the reading must be taken from still another pair of more distal pointers 116 in window 110, because these pointers are at a higher location on the tube 22 calibrated with reference to precise degree of foreshortening of the overall length of probe assembly 44 (it is now shorter than at position A and position B).

Additional width measurements may be obtained by using other disposable probe assemblies in which the wings 50 are of greater width at the semi-expanded and fully-expanded foreshortening rod 46 positions.

The shape of the uterus can be graphically plotted, as illustrated in FIG. 19. To this end, when the overall length measurement is made as described above, the overall length is plotted as with a dashed line 120 between reference line 28 and line 100A indicating the level of the fundus 100. Thereafter, when the first smaller width profile is measured indicating the position of the isthmus, the insertion depth which is read off against the scale marking 106 on the face of the key 102 is noted at point 122, and the known wingspread of wings 50 is plotted as line 124. Thus effective length of the cervix is determined to be the distance between line 28 and line 124, and the length of the endometrial cavity is the distance between line 124 and line 100A. When the second greater width measurement is taken, the depth that is read off the scale 106 is plotted at point 126. The known wing span of wings 50, which are now in their fully expanded position, is plotted as line 128. In a graphical manner, the shape of the endometrial cavity can now be extrapolated by extending two lines, each of which lies along the ends of lines 124 and 128 and each of which intersects line 100A, defining line 130 (which is a portion of line 100A) and which line 130 represents the approximate width of the fundus. It can be seen that this graphical shape will be to scale, because lines 124 and 128 are scaled from known quantities, while line 120 and points 122 and 126 have been measured and are plotted in accordance with such measurement.

Figure 5:
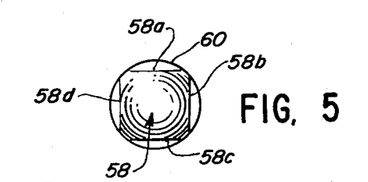
FIG. 5 is an end elevation of the same control button.

In order to help the gynecologist keep track of which set of pointers 112, 114 or 116 should be used at each step of the measuring procedure, advantage is taken of the fact that the control push-button 58 rotates (along with the cam barrel 60) each time the cam mechanism 56 steps to a new wing-actuating or wing-retracting position. The bottom 58 has a polygonal cross-sectional shape (see FIG. 5), giving it a plurality of discrete faces 58a through 58d which move successively into an upwardly facing position (i.e., into alignment with the read-out windows 108 and 110) as the button 58 steps through its sequence of operating positions along with cam barrel 60. Each face 58a–d is marked in some distinctive fashion, as by color-coding, numbering or the like; and a similar marking is placed next to the particular set of pointers 112, 114 or 116 which should be used whenever that face of the bottom 58 is presented. Then all the gynecologist must do, to make sure that the right set of pointers is being read at any given time, is to select that set of pointers whose marking corresponds to whichever face of bottom 58 which is currrently presented.

The final position of the cam barrel 60 again restores the link 64 and rod 46 to their original fully extended positions, thus fully retracting the wings 50 to permit total withdrawal of the instrument from the uterus and vagina.

Although the preferred embodiment has been described, it is evident that a greater number of width measurements could be accommodated by simply providing a larger number of stable positions of the cam barrel 60 (and an equal number of faces on the bottom 58, if desired).

Another design alternative which should be noted is that the wings 50 may be provided with specially formed scraping edges 118 preferably made of metal, such as stainless steel, as seen in FIG. 6A, so that they may be used for collecting cellular material, curetting or scraping the epithelial lining of the endometrial cavity and endocervical canal. When wing panels are closed as the instrument is withdrawn from the uterus following curettage, the scraped tissues are retained inside the wings. In order to allow more tissues to be retained within the wing structure, the lower wings are formed with a smaller diameter 132.

In order to improve the usefulness of the instrument when used for the purpose of uterine cancer screening, a small sleeve 134 made of cotton or a synthetic material, such as polyester, is fitted over a recessed portion of wing-forming sleeve 44 proximal to the wing panels. The fabric sleeve collects and retains cellular material from the endometrial cavity and cervical canal as it comes in contact with their epithelial lining. After the instrument is withdrawn from the uterus, the material collected on the sleeve is spread over slides which are processed as "Pap" smears.

It will now be appreciated that this invention provides an improved instrument which does a more complete job than its predecessors. When used as a uterine measuring device, it gives a fuller picture of the width profile by providing plural width measurements as well as axial measurements. Or when used as a tissue sampling or curette device, there, too, it is capable of scraping the uterine lining with a plurality of extended wings providing different curette sizes. Moreover, the additional mechanism required to establish a plurality of stable probe insertion positions and wing extensions need not be discarded before its useful life is over, as the handle assembly may form a permanent mechanism from which the disposable probe assembly, as well as the reading tube, may be removed and replaced.

Although an illustrative embodiment of the invention has been shown and described, it is to be understood that various modifications and substitutions may be made by those skilled in the art without departing from the novel spirit and scope of the present invention.

What is claimed is:

1. In an intra-uterine instrument of the type having a handle assembly and a probe assembly mounted on said handle assembly and extending in a longitudinal direction for insertion into a uterus, said probe assembly including foreshortening means and a wing-forming member which is secured to said foreshortening means and which is operable to collapse outwardly into a laterally winged configuration when foreshortened, so that said wings may contact the walls of the uterus, the improvement comprising:

actuating means mounted on said handle assembly and operatively engaging said foreshortening means for establishing a plurality of separate stable operating positions for said foreshortening means, including one position in which said wing-forming member is foreshortened thereby to a fraction of its undeformed length, whereby said wings project a first distance laterally, and another position in which said wing-forming member is foreshortened thereby to another fraction of its undeformed length, larger than said first fraction, whereby said wings project a second distance laterally, greater than said first distance, so that said wings contact said uterine walls at positions of greater and lesser insertions of said probe assembly into said uterus.

2. An intra-uterine instrument as in claim 1, wherein said actuating means comprises an actuating link, means mounting said actuating link on said handle assembly for reciprocation in said longitudinal directions, and a movement for controlling such reciprocation and establishing at least said two stable operating positions for said actuating link at different locations along the path of said reciprocation.

3. An intra-uterine instrument as in claim 2, further comprising interengaging means on said wing-forming member and on said handle assembly for removably and replaceably locking them together and interengaging means on said foreshortening member and said actuating link for removably and replaceably locking them together for conjoint reciprocation relative to said handle assembly and said wing-forming member whereby to accomplish foreshortening of said wing-forming member, and whereby said interengaging means make said entire probe assembly removable and replacable relative to said intra-uterine instrument.

4. An intra-uterine instrument as in claim 2, wherein said control movement is of the spring-biased, rotary cam, push-button-operated type.

5. An intra-uterine instrument as in claim 1, further comprising reading means, means supporting said handle assembly on said reading means for translation relative thereto in said longitudinal direction, means on said handle assembly and on said reading means cooperating to indicate the depth of insertion of said probe into the uterus in various positions of translation of said handle assembly relative to said reading means, and including at least first depth indicating means calibrated with reference to the effective length of said probe assembly in one wing means extension position and second depth indicating means calibrated with reference to the effective length of said probe assembly in the other extension position.

6. An intra-uterine instrument as in claim 5, wherein said actuating means comprises a sequence indicator member arranged to move to two different sequence indicating positions when said foreshortening means move to said two operating positions respectively, sequence marking means on said sequence indicator member alternately presented in said two different sequence indicating position, and two sequence marking means associated with said two indicating means respectively and correlated with said sequence marking means on said sequence indicator member in a manner to indicate that said first depth indicating means is in its sequence indicating position, and said second depth indicating means is to be read when said sequence indicating means is in its sequence indicating position.

7. An intra-uterine instrument as in claim 6, wherein said actuating mechanism comprises a spring-biased, rotary cam, push-button movement, and said sequence indicating member is operatively associated therewith to rotate to two different angular positions to present two different surface areas when said fore-shortening means actuator is in said two different operating positions respectively, and said first and second sequence marking means are on said two different surface areas respectively.

8. An intra-uterine instrument comprising:
a reading tube suitable for insertion into a vagina and into abutment with a cervix;
a handle assembly including a handle tube reciprocable longitudinally within said reading tube;
a probe assembly mounted on a distal end of said handle assembly and extending longitudinally therefrom for insertion into a uterus when said handle assembly is reciprocated relative to said reading tube;
said probe assembly including a wing-forming sleeve of relatively flexible material and a foreshortening rod reciprocable longitudinally within said wing-forming sleeve and secured thereto at a distal location whereby reciprocation of said foreshortening rod foreshortens said wing-forming sleeve and consequently collapses the flexible material thereof laterally outwardly at a less distal location to form laterally outwardly extending wings for contact with the inner walls of said uterus;
interengaging means on said wing-forming sleeve and said handle tube for removably and replaceably connecting them for conjoint reciprocation relative to said reading tube;
said interengaging means on said foreshortening rod comprising a flange secured thereto;
said interengaging means on said actuating link comprising a receptacle adapted to receive said foreshortening rod flange upon insertion thereof in a lateral direction;
said interengaging means on said wing-forming sleeve comprising a flange secured thereto;
and said interengaging means on said handle tube comprising a bifurcation of said tube, one branch of said bifurcation having a receptacle secured thereto which is adapted to receive said wing-forming sleeve flange upon insertion thereof in a lateral direction, the other branch of said bifurcation comprising a member hinged to said handle tube and rotatable laterally therefrom to provide an access opening for lateral insertion of said flanges into said respective receptacles, and rotatable laterally toward said handle tube to reclose said access opening for locking said flanges into said respective receptacles after insertion;
said handle assembly comprising an actuating mechanism including an actuating link reciprocable within said handle tube and connected for reciprocating said foreshortening rod relative to said handle tube and wing-forming sleeve whereby to accomplish foreshortening;
and interengaging means on said foreshortening rod and said actuating link removably and replaceably connecting them for conjoint reciprocation relative to said handle tube and said wing-forming sleeve;
whereby said entire probe assembly is removable and replaceable relative to said handle assembly.

9. An intra-uterine instrument comprising:
a reading tube suitable for insertion into a vagina and into abutment with a cervix;
a handle assembly including a handle tube reciprocable longitudinally within said reading tube;
a probe assembly mounted on a distal end of said handle assembly and extending longitudinally therefrom for insertion into a uterus when said handle assembly is reciprocated relative to said reading tube;
said probe assembly including a wing-forming sleeve of relatively flexible material and a foreshortening rod reciprocable longitudinally within said wing-forming sleeve and secured thereto at a distal location whereby reciprocation of said foreshortening rod foreshortens said wing-forming sleeve and consequently collapses the flexible material laterally outwardly at a less distal location to form laterally outwardly extending wings for contact with the inner walls of said uterus;
said handle assembly comprising an actuating mechanism including an actuating link reciprocable within said handle tube and connected for reciprocating said foreshortening rod relative to said handle tube and wing-forming sleeve whereby to accomplish foreshortening;
said actuating mechanism also including a spring-biased, rotary cam, push-button control movement for establishing at least one stable position of reciprocation of said actuating member wherein said foreshortening rod is sufficiently retracted in the proximal direction to extend said wings.

10. An intra-uterine instrument as in claim 9, further comprising window means on said reading tube and marking means on said handle tube cooperating to indicate the degree of insertion of said probe assembly into said uterus.

11. An intra-uterine instrument as in claim 10, wherein said window means and marking means comprise first window means and first marking means cooperating with each other to indicate at which uterine width matches one lateral spread of said wings, and second window means and second marking means cooperating with each other to indicate at which uterine depth the uterine width matches another lateral spread of said wings.

12. An intra-uterine instrument as in claim 11, wherein said control movement comprises a control pushbutton extending from the proximal end of said handle tube, and rotating with said rotary cam, a first matching pair of sequence-indicating markings, one of which appears adjacent said first window means and the other of which appears on that surface of said control button which rotates into alignment with said window means when one wing span is in effect, and a second matching pair of sequence-indicating markings, one of which appears adjacent said second window means and the other of which appears on that surface of said control button which rotates into alignment with said window means when another wing span is in effect.

13. An intra-uterine instrument as in claim 12, wherein said window means and marking means comprise third window means and third marking cooperating with each other to indicate the depth of said uterus when said probe is sufficiently extended to contact the fundus thereof.

* * * * *